(12) United States Patent
Simms

(10) Patent No.: US 8,156,941 B1
(45) Date of Patent: Apr. 17, 2012

(54) HEEL OFFLOADING ABDUCTOR PILLOW

(76) Inventor: Jessica Simms, Pembroke Pines, FL (US)

( * ) Notice: Subject to any disclaimer, the term of this patent is extended or adjusted under 35 U.S.C. 154(b) by 170 days.

(21) Appl. No.: 12/244,540

(22) Filed: Oct. 2, 2008

(51) Int. Cl.
*A61F 5/37* (2006.01)
*A61G 15/00* (2006.01)
*A47C 17/86* (2006.01)

(52) U.S. Cl. .............................. 128/882; 5/648; 128/845

(58) Field of Classification Search .................. 128/882, 128/869, 845; 5/648, 650, 734, 632; 602/24, 602/28, 23
See application file for complete search history.

(56) References Cited

U.S. PATENT DOCUMENTS

| | | | | |
|---|---|---|---|---|
| 3,717,144 A * | 2/1973 | Bimler | ............................ | 602/16 |
| 4,372,299 A * | 2/1983 | Fixel | ............................... | 602/24 |
| 4,805,605 A * | 2/1989 | Glassman | ....................... | 602/24 |
| 5,117,522 A * | 6/1992 | Everett | ................................ | 5/648 |
| 5,449,339 A * | 9/1995 | Drennan | ......................... | 602/23 |
| 5,716,334 A * | 2/1998 | Wade | ................................ | 602/6 |
| 5,725,486 A * | 3/1998 | Engelman | ......................... | 602/5 |
| 5,742,963 A * | 4/1998 | Trevino et al. | ..................... | 5/632 |
| 6,070,585 A * | 6/2000 | Fery et al. | ...................... | 128/845 |
| 6,182,314 B1 * | 2/2001 | Frydman | ............................ | 5/648 |
| 7,536,740 B1 * | 5/2009 | Swartz | ............................... | 5/710 |

* cited by examiner

*Primary Examiner* — Patricia Bianco
*Assistant Examiner* — Victoria J Hicks
(74) *Attorney, Agent, or Firm* — Gold & Rizvi, P.A.; Glenn E. Gold; H. John Rizvi

(57) ABSTRACT

A heel offloading leg abductor pillow which is adapted to relieve pressure from a post-surgical hip patient's heels while supporting the patient's legs in an abducted position includes a generally resilient, wedge-shaped pillow body and a pair of leg support portions carried by the pillow body for supporting a patient's legs, respectively.

21 Claims, 12 Drawing Sheets

HEEL OFFLOADING ABDUCTOR PILLOW

FIELD OF THE INVENTION

The present invention relates to post-surgical leg abduction pillows, which support and position the legs of a post-surgical hip patient in an abducted position for optimal healing. More particularly, the present invention relates to a heel offloading leg abductor pillow, which is adapted to relieve pressure from a post-surgical hip patient's heels while supporting the patient's legs in an abducted position.

BACKGROUND OF THE INVENTION

Management of post-surgical hip patients may include abduction of the patient's legs to prevent dislocation of the hip during recovery. The patient's legs may be maintained in an abducted position by the placement of a wedge-shaped pillow between the legs. A conventional leg abduction pillow is typically a resilient material such as foam rubber, for example, and may include retention straps, which are fastened around the patient's legs above and below the knees, respectively, to secure the pillow in place.

The use of standard leg abduction pillows to maintain the legs of a post-surgical hip patient in an abducted position may require that the only points of contact between the bed in which the patient lies and the patient's leg be at the buttocks and the heel of the foot. Therefore, the heel supports a major portion of the weight of the leg on the bed. This may potentially and commonly cause the formation of ulcers on the heel. Moreover, neurovascular complications can result in the patient's leg distal to the strap.

Therefore, with the growing elderly population, particularly those elderly persons having diabetes (which may result in neuropathy and/or microvascular disease which also predispose a bed bound patient to secondary heel ulcers), a heel offloading leg abductor pillow is needed which is adapted to maintain the legs of a post-surgical hip patient in an abducted position in such a manner that contact pressure between the bed in which the patient lies and the patient's heels is prevented or at least minimized.

SUMMARY OF THE INVENTION

The present invention is generally directed to a heel offloading leg abductor pillow which is adapted to maintain the legs of a post-surgical hip patient in an abducted position while preventing, minimizing, or eliminating the application of support pressure to the patient's heels.

In one aspect of the invention, the heel offloading leg abductor pillow comprises:
a generally resilient, wedge-shaped pillow body; and
a pair of leg support portions carried by the pillow body.

In yet another aspect of the invention, a proximal strap opening and a pair of spaced-apart distal strap slots may extend through the pillow body, and a pair of proximal leg straps may extend through the proximal strap opening and a pair of distal leg straps may extend through the pair of distal strap slots, respectively.

In another aspect of the invention, a pair of spaced-apart proximal strap slots and a pair of spaced-apart distal strap slots may extend through the pillow body and a pair of proximal leg straps may extend through the proximal strap slots, respectively, and a pair of distal leg straps may extend through the pair of distal strap slots, respectively.

In yet another aspect of the invention, the pillow body may include a proximal end, a pair of side surfaces diverging from the proximal end and a distal end extending between the side surfaces, and the pair of leg support portions may be carried by the pair of side surfaces, respectively.

In still another aspect of the invention, a proximal cavity may be provided in the proximal end of the pillow body.

In another aspect of the invention, each of the pair of leg support portions may be integral with the pillow body.

In yet another aspect of the invention, each of the pair of leg support portions may be positionally adjustable on the pillow body.

In a still further aspect of the invention, each of the pair of leg support portions may include a leg support bottom extending from the pillow body and a leg support outer sidewall may extend from the leg support bottom, and the leg trough may be provided in the leg support bottom and the leg support outer sidewall.

In another aspect of the invention, the lower legs can be elevated to assist with venous drainage via varying degrees of graduated foam (or similar) within the leg support portion of the apparatus.

While yet another aspect incorporates a foot drop strap disposed upon a distal end of the leg support.

These and other aspects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

DETAILED DESCRIPTION OF THE PREFERRED EMBODIMENTS

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the invention and are not intended to limit the scope of the invention, which is defined by the claims. Furthermore, there is no intention to be bound by any expressed or implied theory presented in the preceding technical field, background, brief summary or the following detailed description.

Shown throughout the Figures, the present invention is generally directed to a heel offloading leg abductor pillow which is adapted to maintain the legs of a post-surgical hip patient in an abducted position while redistributing pressure away from the heels, and onto the calves, therefore preventing or minimizing the application of support pressure to the patient's heels. An illustrative embodiment of the heel offloading leg abductor pillow includes a generally wedge-shaped pillow body and a pair of leg support portions which are provided on respective sides of the pillow body and are adapted to support the legs of a patient in such a manner that contact pressure between the bed in which the patient lies and the patient's heels is prevented or minimized.

Figure 1:
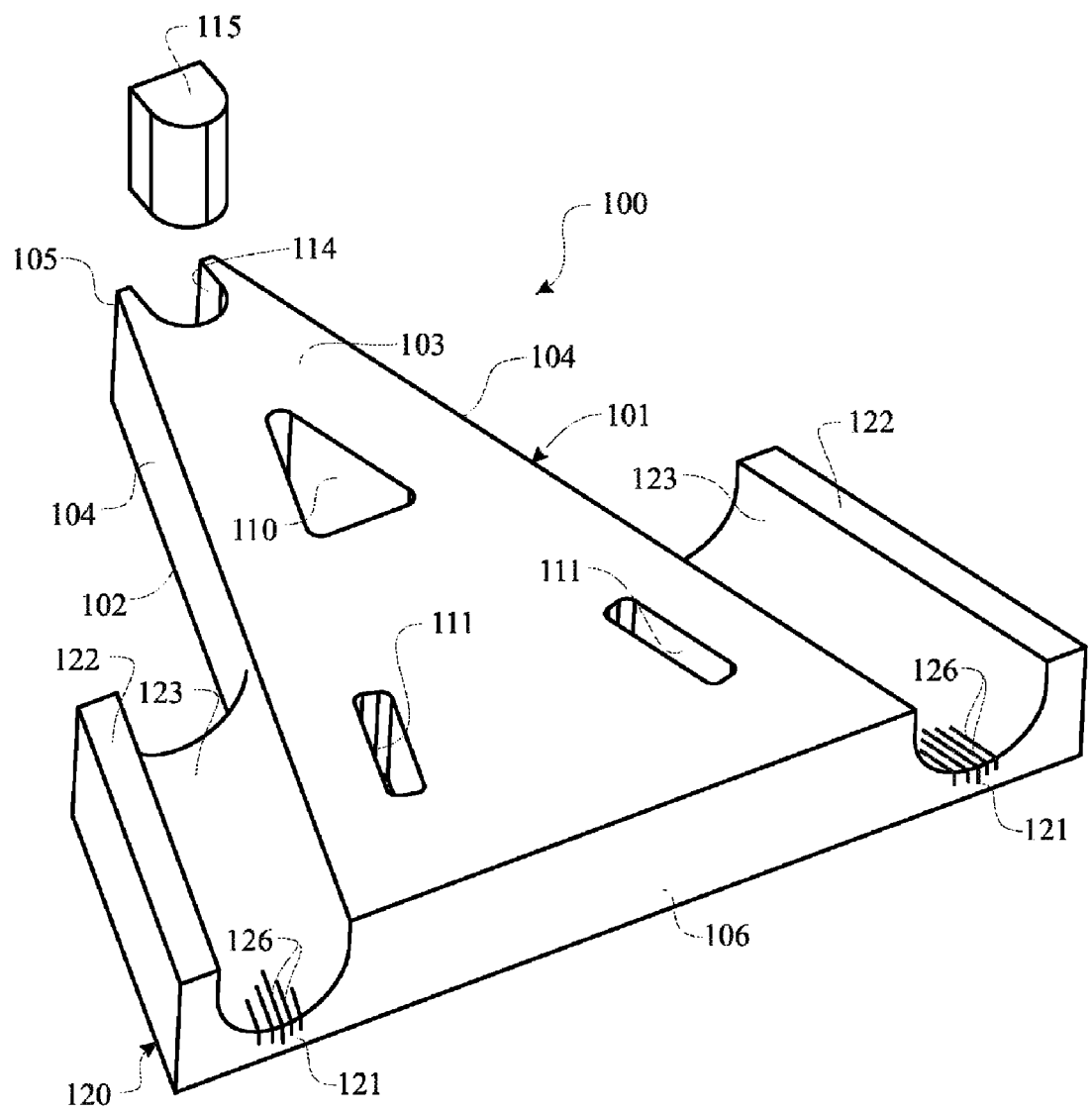
FIG. 1 is a rear exploded perspective view of an illustrative embodiment of a one piece heel offloading leg abductor pillow.

Referring initially to FIG. 1 of the drawings, an illustrative embodiment of the heel offloading leg abductor pillow is generally indicated by reference numeral 100. The heel offloading leg abductor pillow 100 includes a generally elongated, wedge-shaped pillow body 101 which may be a resilient, deformable, fluid-impervious material having a memory such as foam rubber, flame resistant, convoluted material for example and without limitation. In some embodiments, the pillow body 101 may include a layer of memory foam or pressure redistribution foam. In some embodiments, the pillow body 101 may be a flame-resistant, convoluted material.

In some embodiments, the pillow body 101 may be Latex-free. The pillow body 101 has a generally flat or planar bottom surface 102, a generally flat or planar top surface 103 and a pair of generally flat or planar side surfaces 104 which diverge from a proximal end 105 to a distal end 106, the proximal end 105 being narrower than the distal end 106. The pair of generally flat or planar side surfaces 104 could be of any various foam types, such as those mentioned above. In some embodiments, a proximal cavity 114 may extend into the proximal end 105 of the pillow body 101 for purposes, which will be hereinafter described. A proximal cavity insert 115 may be detachably inserted in the proximal cavity 114 when the proximal cavity 114 is not in use. A proximal strap opening 110, which may have a generally triangular shape, as illustrated, extends through the pillow body 101 generally adjacent to the proximal end 105. A pair of spaced-apart distal strap slots 111 extends through the pillow body 101 generally adjacent to the distal end 106 for purposes, which will be hereinafter described.

A leg support portion 120 is provided on each side surface 104 of the pillow body 101. Each leg support portion 120 may be the same material as or a different material than that of the pillow body 101. Each leg support portion 120 may extend along the corresponding side surface 104 from the distal end 106 to generally about midway between the proximal end 105 and the distal end 106 of the pillow body 101. In some embodiments, each leg support portion 120 may be integral with the pillow body 101. Each leg support portion 120 may include a leg support bottom 121, which extends from the corresponding side surface 104. A leg support outer sidewall 122 extends from the leg support bottom 121, in generally spaced-apart and parallel relationship with respect to the corresponding side surface 104 of the pillow body 101. A generally elongated, concave leg support surface, such as a leg trough 123, is provided in the leg support bottom 121 and the leg support outer sidewall 122 of each leg support portion 120. The leg trough 123 may have a generally semicircular or U-shaped cross-section, and is preferably fabricated of a conformable or semi-conformable material. In some embodiments, multiple calf and ankle slots 126 extend into the concave surface of the leg trough 123 and the adjoining distal end 106 of the pillow body 101 for purposes, which will be hereinafter described. At least a portion of the leg trough 123 can be fabricated of memory foam or pressure redistribution foam. Foot drop straps (not illustrated) or an extension of foam projecting from a distal end of the leg support portion 120 can be incorporated to support the user's foot to prevent foot drop. The foot drop strap may be attached to the inside or outside of the troughs, without limitation. The foot drop straps can be fabricated including pressure reduction foam, elastic material, non-elastic material, velfoam, rubber or cotton, and without limitation.

Figure 2:
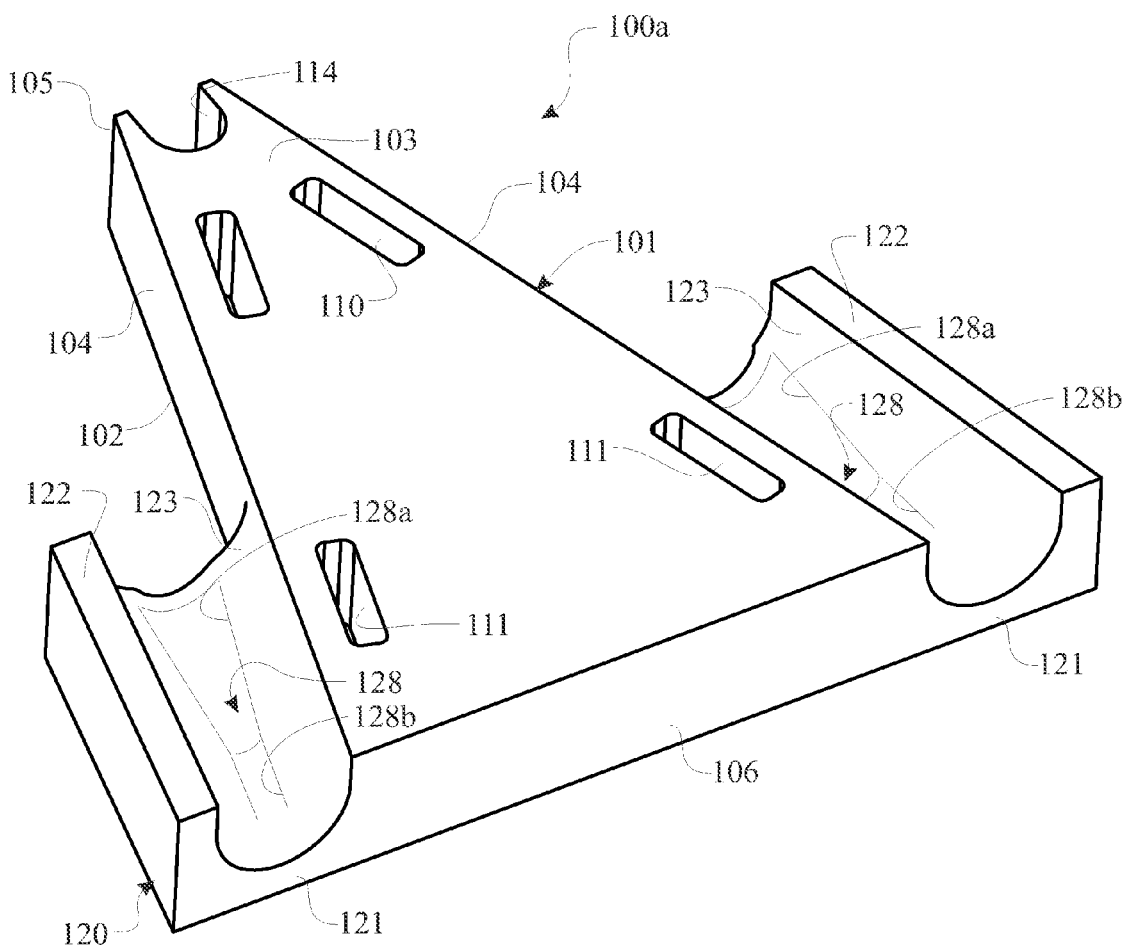
FIG. 2 is rear view of an alternative illustrative embodiment of the heel offloading leg abductor pillow.

Referring next to FIG. 2 of the drawings, an alternative illustrative embodiment of the heel offloading leg abductor pillow 100a is similar in design to the heel offloading leg abductor pillow 100, which was heretofore described with respect to FIG. 1, except a generally elongated calf/ankle cavity 128 extends into the concave surface of each leg trough 123. Each calf/ankle cavity 128 may have a calf portion 128a, which generally corresponds to the posterior calf portion of a patient's leg, and an ankle portion 128b, which generally corresponds to the posterior ankle portion of the patient's leg. The purpose of each calf/ankle cavity 128 will be hereinafter described. In some embodiments, a pair of generally elongated, rectangular, spaced-apart proximal strap slots 112 may extend through the pillow body 101 generally adjacent to the proximal end 105 thereof. In other embodiments, a generally triangular proximal strap opening 110 may extend through the pillow body 101 as was heretofore described with respect to the heel offloading leg abductor pillow 100 in FIG. 1.

Figure 3:
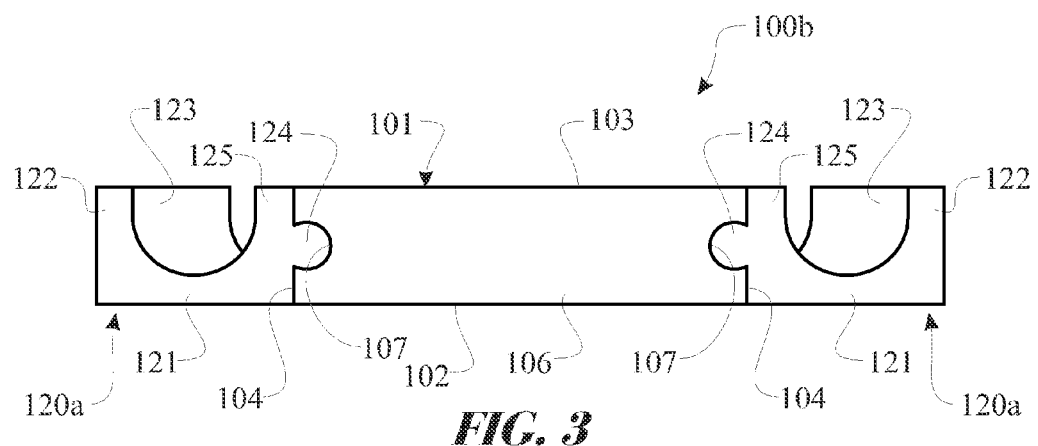
FIG. 3 is a rear view of another alternative illustrative embodiment of the heel offloading leg abductor pillow.
Figure 4:
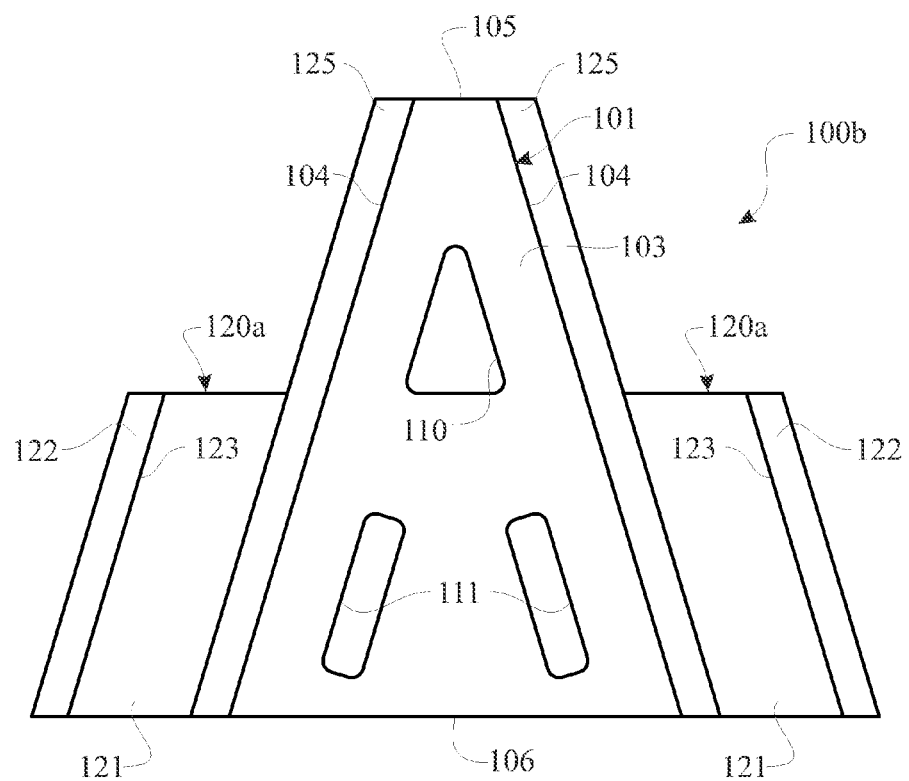
FIG. 4 is a top view of the heel offloading leg abductor pillow illustrated in FIG. 3.

Referring next to FIGS. 3, 4, 7, 8 and 16 of the drawings, another alternative illustrative embodiment of the heel offloading leg abductor pillow is generally indicated by reference numeral 100b. A leg support portion 120a of the heel offloading leg abductor pillow 100b is positionally adjustable along each side surface 104 of the pillow body 101. As illustrated in FIGS. 3 and 4, each leg support portion 120a includes an elongated leg support inner sidewall 125, which adjustably engages the corresponding side surface 104 of the pillow body 101 typically in a manner, which will be hereinafter described. A leg support bottom 121 extends outwardly from the leg support inner sidewall 125. A leg support outer sidewall 122 extends from the leg support bottom 121, in generally spaced-apart and parallel relationship with respect to the leg support inner sidewall 125. A generally elongated, concave leg trough 123, which may have a generally semicircular cross-section, extends along the leg support inner sidewall 125; the leg support bottom 121; and the leg support outer sidewall 122. As illustrated in FIG. 4, in some embodiments the leg support inner sidewall 125 may be generally coextensive with the corresponding side surface 104 of the pillow body 101, whereas the leg support outer sidewall 122 may correspond to about the rear half of the leg support inner sidewall 125.

Figure 7:
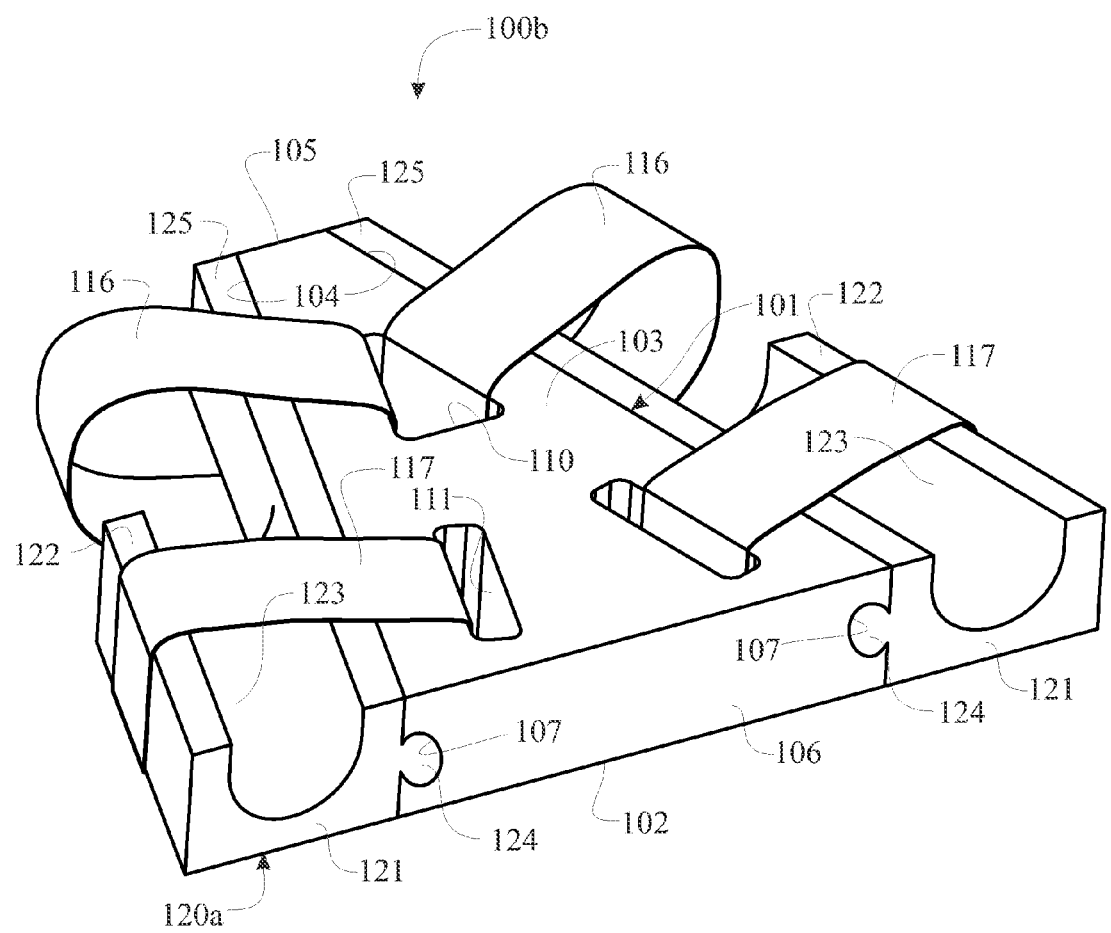
FIG. 7 is a rear perspective view of the heel offloading leg abductor pillow illustrated in FIGS. 5 and 6, fitted with proximal and distal leg straps.
Figure 16:
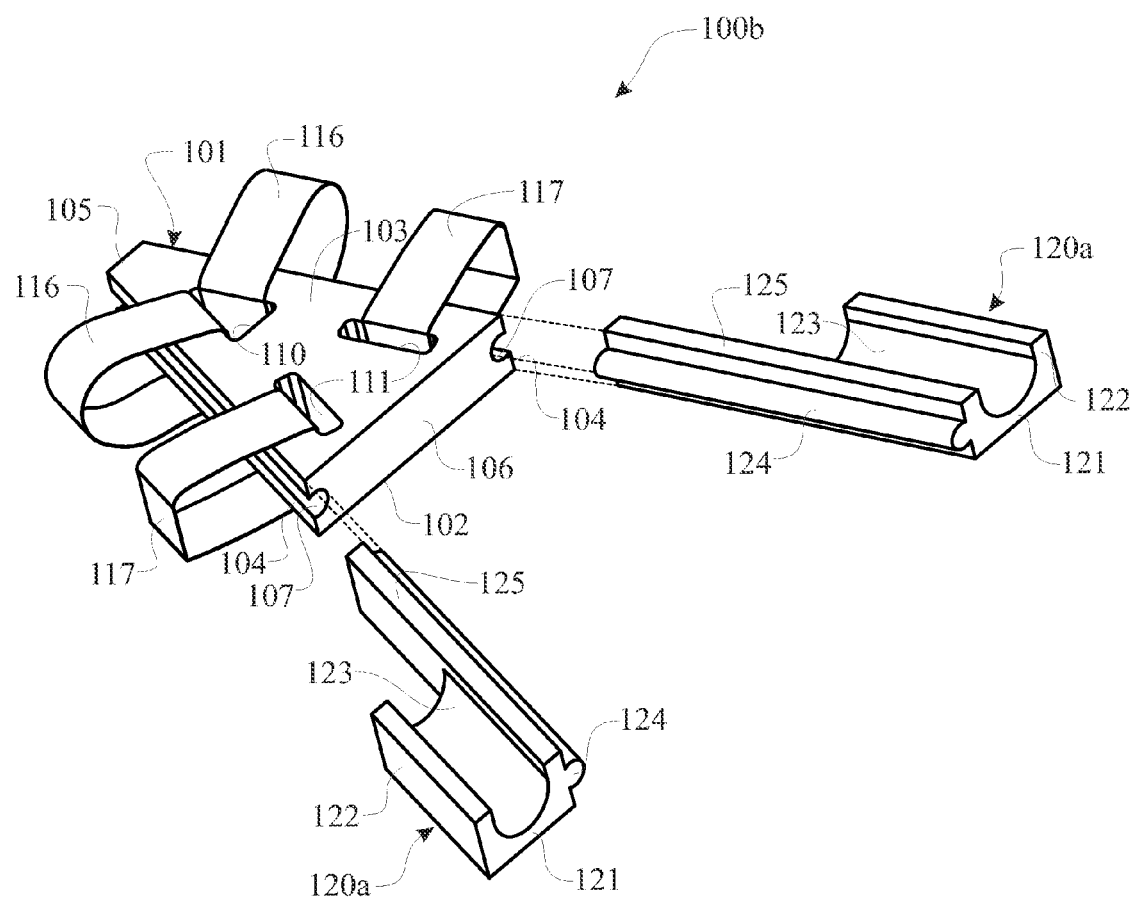
FIG. 16 is an exploded perspective view of the heel offloading leg abductor pillow illustrated in FIGS. 3 and 4.

The leg support inner sidewall 125 of each leg support portion 120a may adjustably engage the corresponding side surface 104 of the pillow body 101 according to any suitable technique, which is known by those skilled in the art. As illustrated in FIGS. 3, 7 and 16, in some embodiments an elongated attachment slot 107 extends into and along each side surface 104 of the pillow body 101. A correspondingly shaped attachment tab 124 extends from the leg support inner sidewall 125 of each leg support portion 120a and interlocks with the attachment slot 107. Accordingly, as illustrated in FIG. 16, the attachment tab 124 of each leg support portion 120a is slidably inserted in the companion attachment slot 107 to facilitate adjustment of each leg support portion 120a to a selected position along the corresponding side surface 104 of the pillow body 101. This may be carried out to adjust the length of the heel offloading leg abductor pillow 100b to accommodate the length of the legs 133 of the patient 132. It is recognized that other adjustable interfaces such as a dense hook and loop tape (commonly referred to as VELCRO), a plurality of pins, a sliding dovetail, mortise and tenons, and the like.

Figure 8:
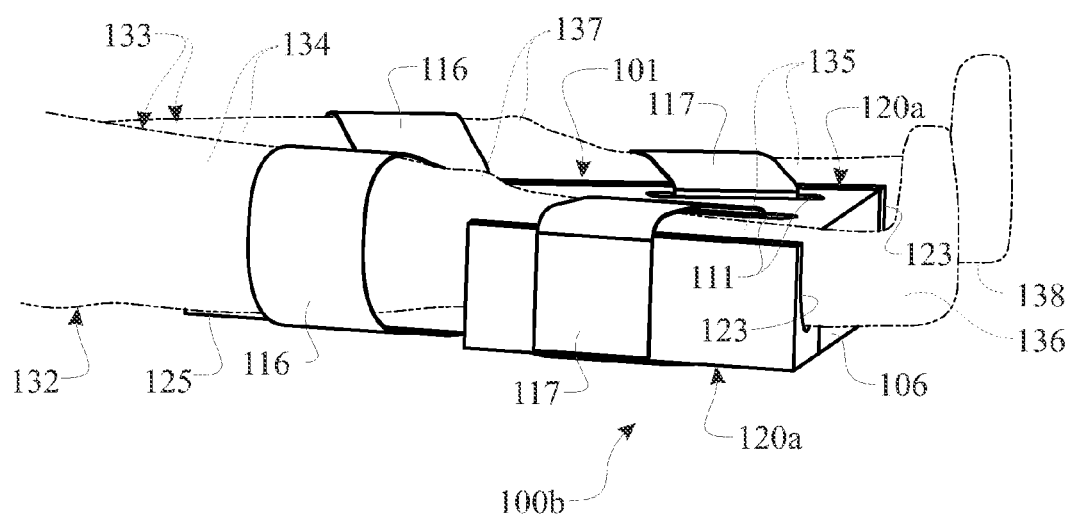
FIG. 8 is a side perspective view of the heel offloading leg abductor pillow illustrated in FIG. 7, attached to legs (illustrated in phantom) of a reclining patient.

As illustrated in FIG. 8, in typical application, the heel offloading leg abductor pillow 100b is suitable for maintaining the legs 133 of a patient 132 (illustrated in phantom) in an abducted position as the patient 132 recovers from hip surgery such as total hip arthroplasty or endoprosthetic hemiarthroplasty, for example and without limitation. Maintaining the legs 133 of the patient 132 in the abducted position may prevent dislocation of the patient's hip during recovery. Accordingly, the wedge-shaped pillow body 101 is placed between the patient's legs 133 with the proximal end 105 of the pillow body 101 disposed at or adjacent to the crotch (not illustrated) of the patient 122 and the distal end 106 of the pillow body 101 disposed between the calves 135 of the patient's legs 133. The calves 135 of the patient's legs 133 rest in the leg troughs 123 of the respective leg support portions 120. The thighs 134 of the patient's legs 133 extend along the respective side surfaces 104 of the pillow body 101, from each leg support portion 120a to the proximal end 105 of the pillow body 101. A pair of proximal leg straps 116 may be extended through the proximal strap opening 110 and around the respective thighs 134 of the patient's legs 133, above each knee 137 and fastened. A pair of distal leg straps 117 may be extended through the respective distal strap slots 111, over the calves 135 below each knee 137 and around the respective leg support portions 120a and fastened. Each proximal leg strap 116 and each distal leg strap 117 may be foam such as Velfoam, rubber or cotton such as cotton comfort band for example and without limitation. As further illustrated in FIG. 8, the ankles 136 of the patient 132 extend beyond the distal end 106 of the pillow body 101 thus, suspending the patient's heels. Furthermore, the leg support bottom 121 of each leg support portion 120a supports the calf 135 of each leg 133. This prevents contact of the patient's heels 138 with a bed (not illustrated) or other support surface on which the patient 132 lies and may also enable the patient 132 to turn his or her feet inwardly or outwardly. The heel offloading leg abductor pillow 100b also may prevent secondary neurovascular complications related to the conventional encircling distal leg straps 117. This is accomplished by cradling the legs 133 of the patient 132 in the leg troughs 123 of the respective leg support portions 120. When applied under the legs 133 of the patient 132, the heel offloading leg abductor pillow 100b flexes and allows the knee 137 of the patient 132 to gatch, providing continued abduction when the patient 132 is placed in a bed or when placed in a chair (not illustrated). It will be appreciated by those skilled in the art that the position of each leg support portion 120a along the corresponding side surface 104 of the pillow body 101 may be selectively adjusted by sliding the attachment tab 124 of each leg support portion 120a in the corresponding attachment slot 107 according to the leg length, comfort, and preference of the patient 132 or care provider to ensure heel suspension is maintained. A foot drop prevention strap (not illustrated) may be fastened to an inner or outer aspect of the pillow body 101 and/or the leg troughs. The foot drop straps are designed such to support the mid plantar foot, providing a means for preventing potential rehabilitation complications such as foot drop, which is related to prolonged bed rest. The leg trough 123 of each leg support portion 120 may taper to the curve of the posterior knee on each leg 133 of the patient 132.

Referring again to FIG. 1 of the drawings, use of the heel offloading leg abductor pillow 100 may be as was heretofore described with respect to use of the heel offloading leg abductor pillow 100b in FIG. 8, except the leg support portions 120 are not adjustable along the respective side surfaces 104 of the pillow body 101. In the heel offloading leg abductor pillow 100, the ankle slots 126 in the leg trough 126 cause the leg support bottom 121 to yield in the event that the patient's ankle 136 (FIG. 8) is rested on the leg support bottom 121. Moreover, in use of the heel offloading leg abductor pillow 100, the proximal cavity insert 115 can be selectively removed from the proximal cavity 114 in the proximal cavity insert 114 of the pillow body 101 to enable urination of a male patient 132 through the proximal cavity 114, as deemed necessary. The proximal cavity 114 may also provide space for perineal care of the patient 132.

Referring again to FIG. 2 of the drawings, use of the heel offloading leg abductor pillow 100a may be as was heretofore described with respect to use of the heel offloading leg abductor pillow 100b in FIG. 8, except the proximal leg straps 116 (FIG. 7) may be extended through the respective proximal strap slots 112 instead of the single proximal strap opening 110, as was heretofore described with respect to the heel offloading leg abductor pillow 100b. In some embodiments, however, the proximal strap opening 110 instead of the proximal strap slots 112 may extend through the pillow body 101, in which case the proximal leg straps 116 are extended through the proximal strap opening 110 as was heretofore described with respect to FIG. 7. Moreover, the calf 135 and the ankle 136 (FIG. 8) of each of the patient's legs 133 rests in the calf portion 128a and the ankle portion 128b, respectively, of each calf/ankle cavity 128 which is provided in the calf/ankle cavity 128 of each leg support portion 120.

Figure 5:
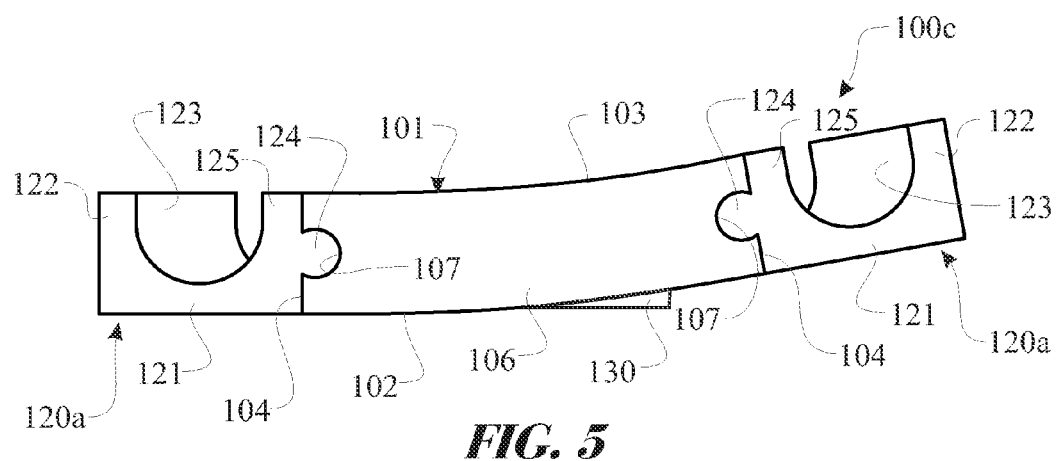
FIG. 5 is a rear view of still another alternative illustrative embodiment of the heel offloading leg abductor pillow, which includes a small positioning wedge.
Figure 6:
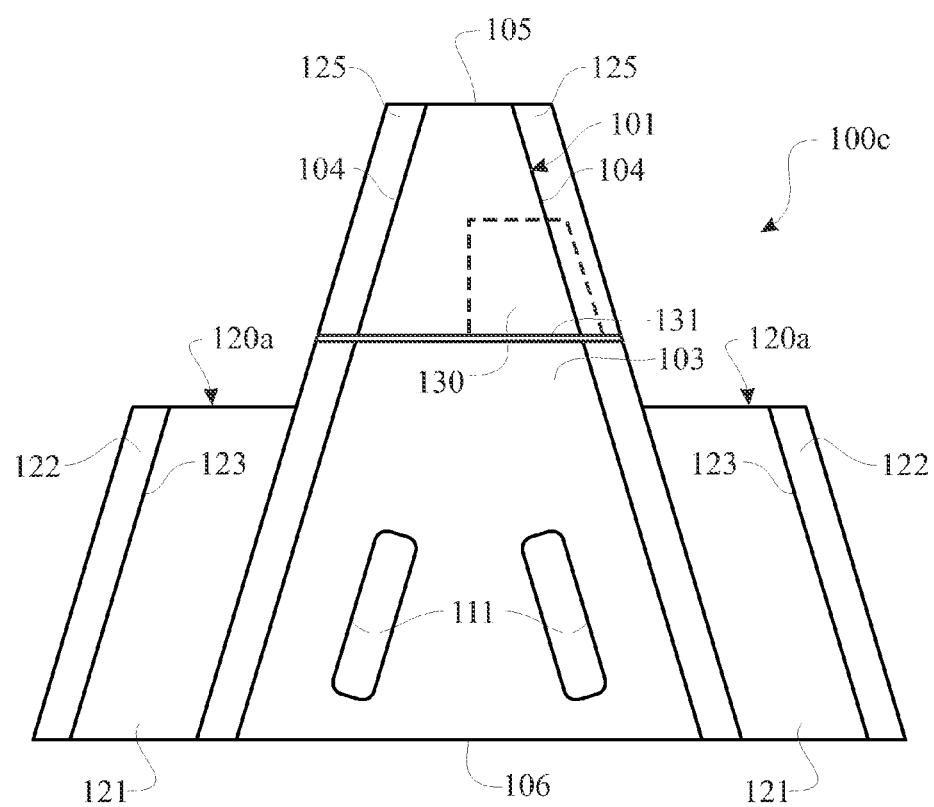
FIG. 6 is top view of the heel offloading leg abductor pillow illustrated in FIG. 5, additionally illustrating the wedge.

Referring next to FIGS. 5 and 6 of the drawings, another alternative illustrative embodiment of the heel offloading leg abductor pillow 100c may be similar in design to the heel offloading leg abductor pillow 100b, which was heretofore described with respect to FIGS. 3, 4, 7, 8 and 16. In the heel offloading leg abductor pillow 100c, however, an elevation wedge 130 is provided (as an example) on the bottom surface 102, generally adjacent to the proximal end 105 of the pillow body 101 to support the posterior flexed knee when the patient is turned and repositioned. As illustrated in FIG. 5, the elevation wedge 130 may have a generally triangular cross-section and elevates one leg support portion 120a with respect to the other leg support portion 120a when the elevation wedge 130 rests on a supporting surface (not illustrated). As illustrated in FIG. 6, a hinge 131 may extend across the pillow body 101 to enable slight elevation of either lateral leg support portion with respect to the remaining portion of the pillow body 101. The elevation wedge 130 facilitates elevation of one hip relative to the other hip of the patient 132 (FIG. 8) (pelvic tilt) as deemed necessary to relieve sacral pressure during post-operative recovery of the bed bound patient 132. The turning process can be facilitated by providing a convex surface along the bottom of the pillow body 101, which will be presented in further detail in FIGS. 13 through 15.

Figure 9:
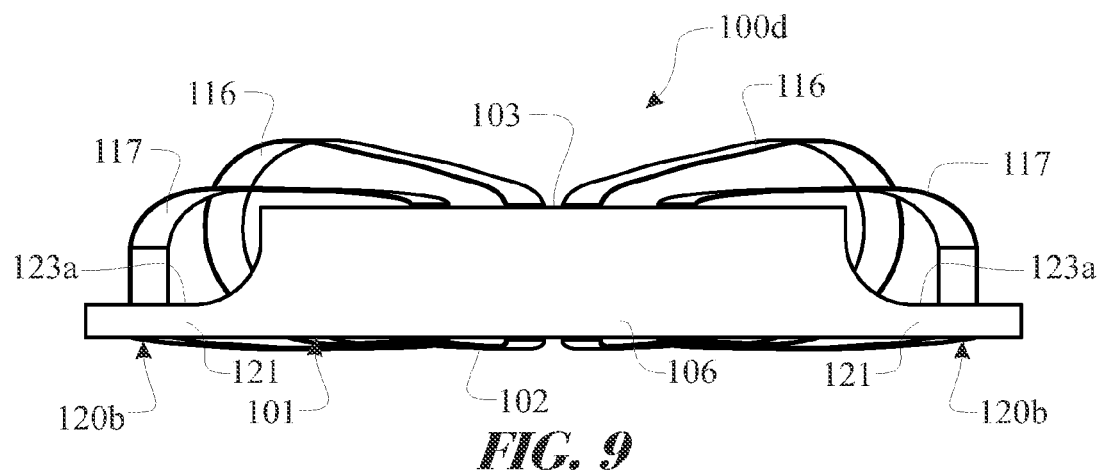
FIG. 9 is a rear view of yet another illustrative embodiment of the heel offloading leg abductor pillow.
Figure 10:
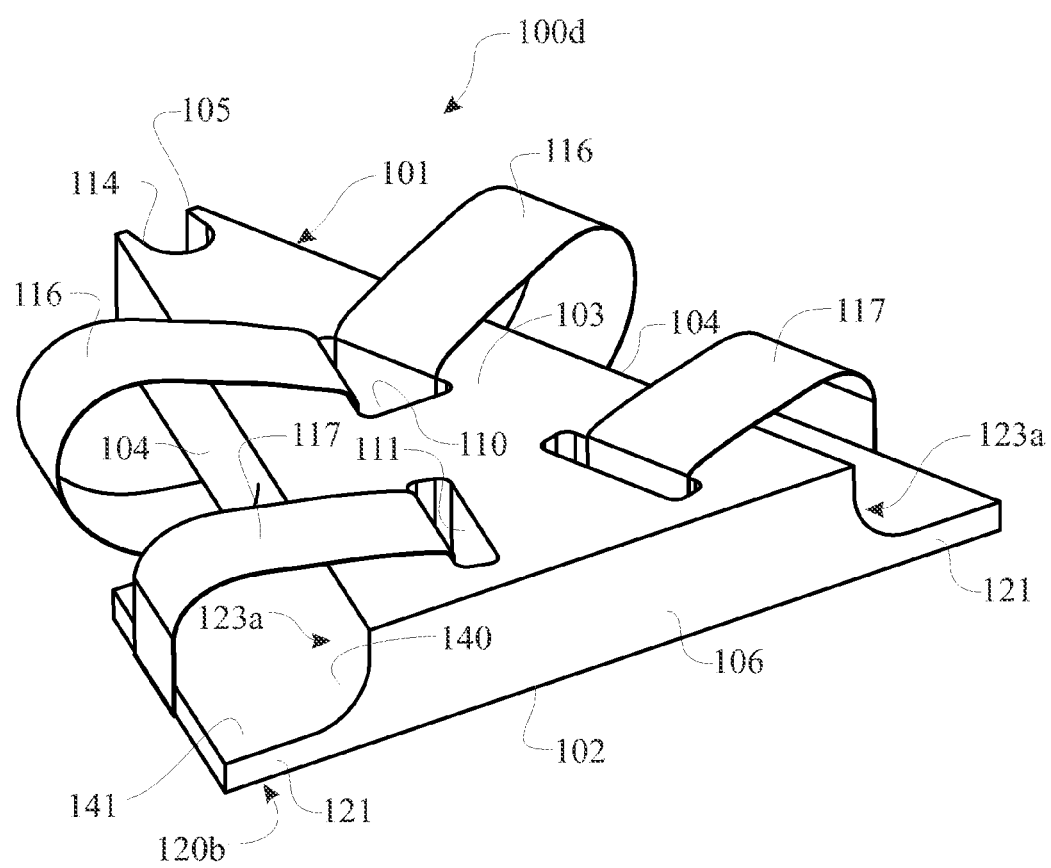
FIG. 10 is a rear perspective view of the heel offloading leg abductor pillow illustrated in FIG. 9.

Referring next to FIGS. 9 and 10 of the drawings, another alternative illustrative embodiment of the heel offloading leg abductor pillow is generally indicated by reference numeral 100d. Each leg support portion 120b of the heel offloading leg abductor pillow 100d includes a concave leg support surface such as a leg notch 123a having a generally rounded inner notch transition surface 140 which extends from the corresponding side surface 104 and a generally flat or planar notch surface 141 which extends outwardly from the notch transition surface 140. In use of the heel offloading leg abductor pillow 100d, which may be as was heretofore described with respect to the heel offloading leg abductor pillow 100b, each calf 135 (FIG. 8) of the patient 132 rests on the inner notch transition surface 140 and the notch surface 141 of each corresponding leg notch 123a.

Figure 11:
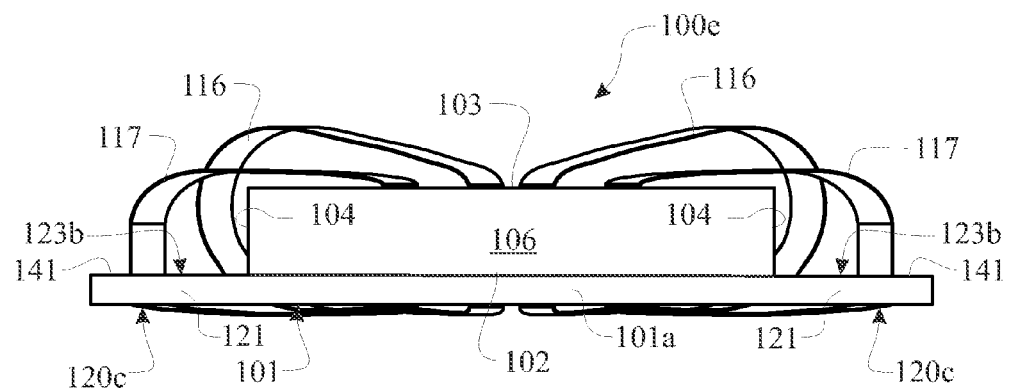
FIG. 11 is a rear view of still another illustrative embodiment of the heel offloading leg abductor pillow.

Referring next to FIG. 11 of the drawings, another alternative illustrative embodiment of the heel offloading leg abductor pillow is generally indicated by reference numeral 100e. Each leg support portion 120c of the heel offloading leg abductor pillow 100e includes a concave leg support surface such as a leg notch 123b having a generally squared-off cross-section in contrast to the rounded cross-section imparted by the rounded inner notch transition surface 140 on the leg support portion 120c of the heel offloading leg abductor pillow 100d in FIGS. 9 and 10. Accordingly, the generally flat or planar side surface 104 of the pillow body 101 may be disposed in generally perpendicular relationship with respect to the generally flat or planar notch surface 141 of the leg support bottom 121. In use of the heel offloading leg abductor pillow 100e, which may be as was heretofore described with respect to the heel offloading leg abductor pillow 100b, each calf 135 (FIG. 8) of the patient 132 rests on the notch surface 141 of each corresponding leg notch 123b. As further illustrated in FIG. 11, in some embodiments, the pillow body 101 may be provided on a pillow body base 101a. Each leg support bottom 121 extends from a corresponding lateral edge of the pillow body base 101a. The pillow body base 101a, incorporating each leg support bottom 121, may be offered as an accessory for the enhancement of the pillow body 101. The pillow body base 101a would be secured to the pillow body 101 via any known means, such as a strap, a dense hook and loop tape, snaps, and the like. Apertures may be provided within the pillow body base 101a, wherein the apertures align with the respective apertures of the pillow body 101. The straps 116, 117 can be used to assist in coupling the pillow body base 101a and the pillow body 101. This would allow a user to provide a heel offloading portion to a standard abduction pillow.

Figure 12:
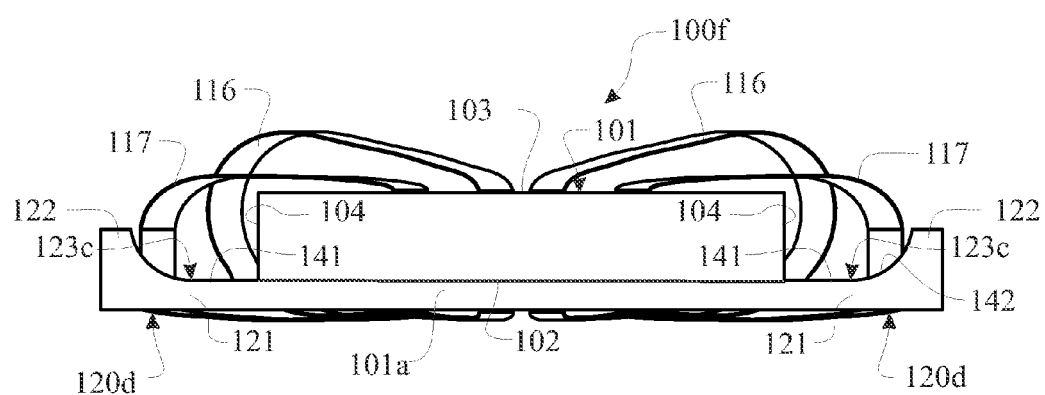
FIG. 12 is a rear view of another illustrative embodiment of the heel offloading leg abductor pillow.

Referring next to FIG. 12 of the drawings, another alternative illustrative embodiment of the heel offloading leg abductor pillow is generally indicated by reference numeral 100f. Each leg support portion 120d of the heel offloading leg abductor pillow 100f includes a concave leg support surface such as a leg notch 123c which is formed by the corresponding side surface 104 of the pillow body 101, the generally flat or planar notch surface 141 which extends from the side surface 104 and a generally rounded outer notch transition surface 142 which extends from the notch surface 141 and onto the inner surface of a leg support outer sidewall 122. In use of the heel offloading leg abductor pillow 100f, which may be as was heretofore described with respect to the heel offloading leg abductor pillow 100b, each calf 135 (FIG. 8) of the patient 132 rests on the notch surface 141 and the outer notch transition surface 142 of each corresponding leg notch 123c. The outer notch transition surface 142 prevents the leg 133 of the patient 132 from rolling out of the leg notch 123c. As further illustrated in FIG. 12, in some embodiments, the pillow body 101 may be provided on a pillow body base 101a and each leg support bottom 121 may extend from a corresponding lateral edge of the pillow body base 101a.

Figure 13:
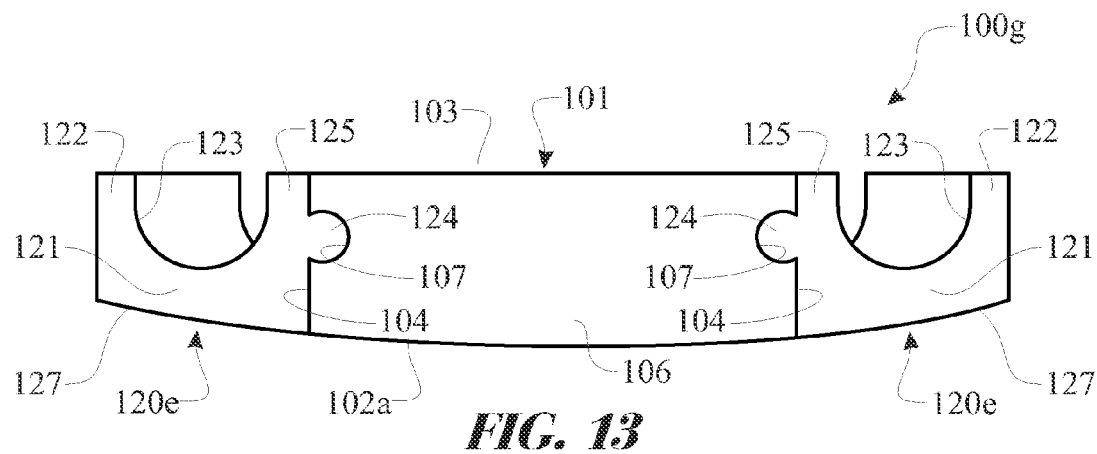
FIG. 13 is a rear view of an alternative illustrative embodiment of the heel offloading leg abductor pillow, having a convex bottom surface.

Referring next to FIG. 13 of the drawings, another alternative illustrative embodiment of the heel offloading leg abductor pillow 100g includes a pillow body 101 having a generally convex bottom surface 102a. The bottom surfaces 127 of the respective leg support portions 120e may also be convex. Accordingly, the heel offloading leg abductor pillow 100g is capable of tilting or rocking in a side-to-side motion when the bottom surface 102a of the pillow body 101 rests on a flat supporting surface (not illustrated) and the patient's legs 133 (FIG. 8) are secured in the respective leg troughs 123.

Figure 14:
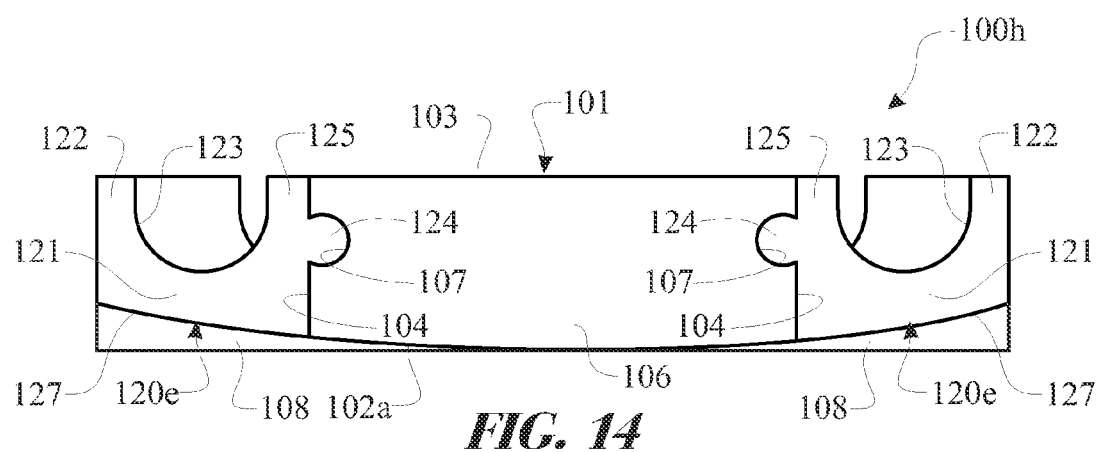
FIG. 14 is a rear view of another alternative illustrative embodiment of the heel offloading leg abductor pillow, having a convex bottom surface which fits into a resilient pillow base.

Referring next to FIG. 14 of the drawings, another alternative illustrative embodiment of the heel offloading leg abductor pillow 100h includes a resilient pillow base 108 which is provided on the convex bottom surface 102a and on the convex bottom surfaces 127 of the respective leg support portions 120e. Accordingly, the pillow base 108 limits the side-to-side rocking motion of the heel offloading leg abductor pillow 100h when the pillow base 108 rests on a flat supporting surface (not illustrated) and the patient's legs 133 (FIG. 8) are secured in the respective leg troughs 123.

Figure 15:
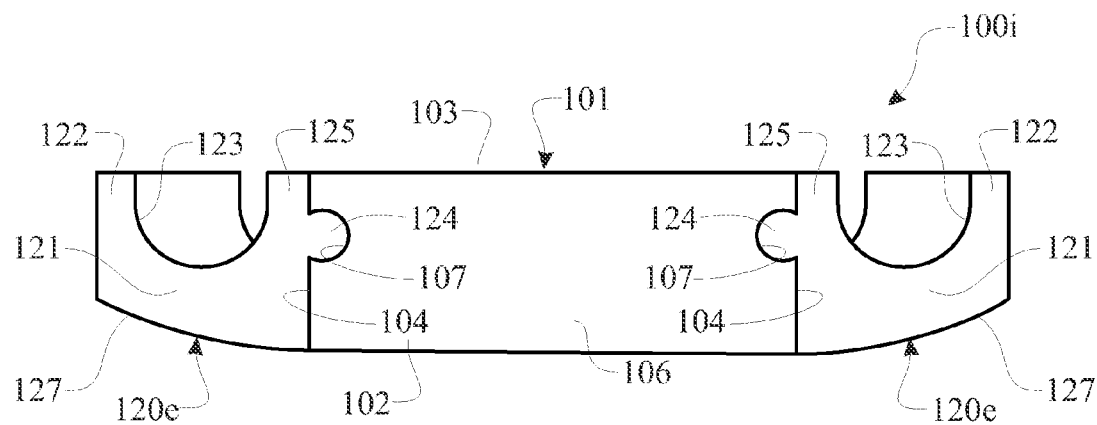
FIG. 15 is a rear view of still another alternative illustrative embodiment of the heel offloading leg abductor pillow, having a flat pillow body bottom surface and convex leg support portion bottom surfaces.

Referring next to FIG. 15 of the drawings, another alternative illustrative embodiment of the heel offloading leg abductor pillow 100i includes a pillow body 101 having a generally flat or planar bottom surface 102a. The bottom surfaces 127 of the respective leg support portions 120e may be convex. Accordingly, while the patient's legs 133 (FIG. 8) are secured in the respective leg troughs 123, the heel offloading leg abductor pillow 100g remains stationary when the bottom surface 102 rests on a flat supporting surface (not illustrated) and tilts when the bottom surface 127 of either leg support portion 120e rests on the supporting surface. Each of the embodiments of the heel offloading leg abductor pillows 100g, 100h, and 100i can utilize the elevation wedge 130 for elevating the patient's hip, utilizing the shaped bottom of the pillow to assist in rolling the pillow.

Figure 17A:
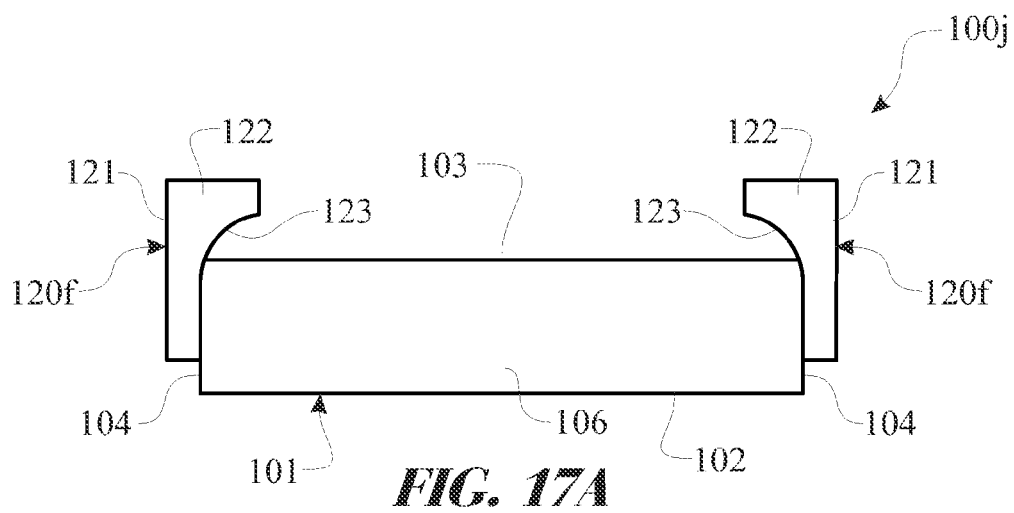
FIG. 17A is a rear view of yet another illustrative embodiment of the heel offloading leg abductor pillow, with the leg support portions disposed in a raised position with respect to the pillow body.
Figure 17B:
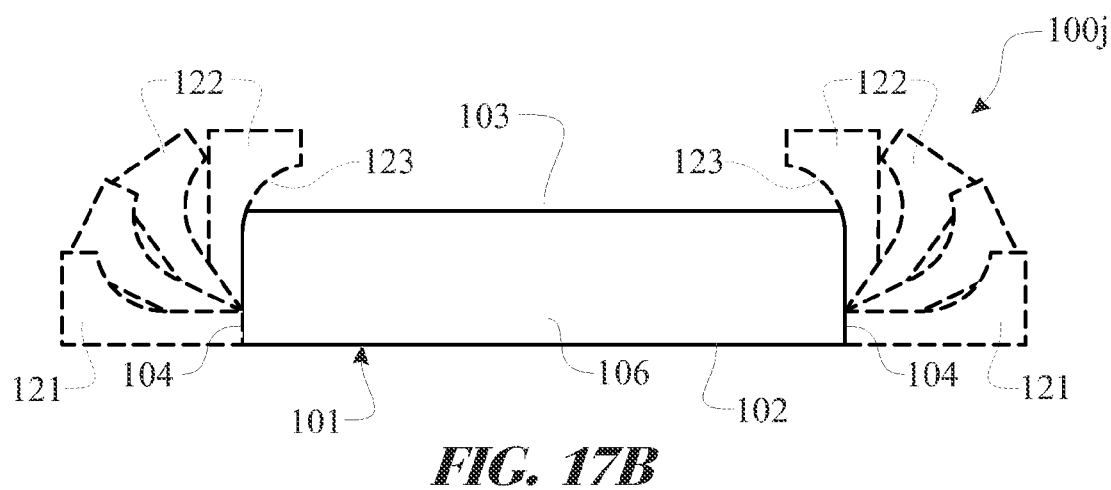
FIG. 17B is a rear view of the heel offloading leg abductor pillow illustrated in FIG. 17A, more particularly illustrating multi-positioning capability of the leg support portions with respect to the pillow body.
Figure 17C:
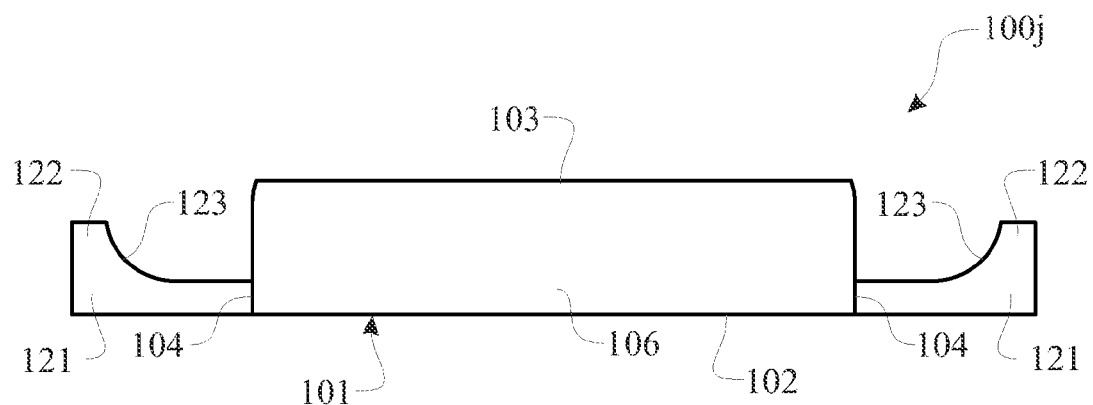
FIG. 17C is a rear view of the heel offloading leg abductor pillow illustrated in FIG. 17A, with the leg support portions disposed in a lowered position with respect to the pillow body.

Referring next to FIGS. 17A-17C of the drawings, another alternative illustrative embodiment of the heel offloading leg abductor pillow 100*j* includes a leg support portion 120*f* which may be flexibly attached to the corresponding side surface 104 of the pillow body 101 such as by using a strip of fabric (not illustrated), for example and without limitation. Accordingly, as illustrated in FIG. 17*b*, the leg support portions 120*f* are capable of being selectively deployed in a raised or folded configuration, as illustrated in FIG. 17A, for storage purposes or simply for patients comfort and ease in repositioning, by allowing the patient to fully bend the knee of the unaffected side. The leg support portions 120*f* can be selectively deployed in a lowered or extended, functional configuration, as illustrated in FIG. 17C, for use.

Figure 18:
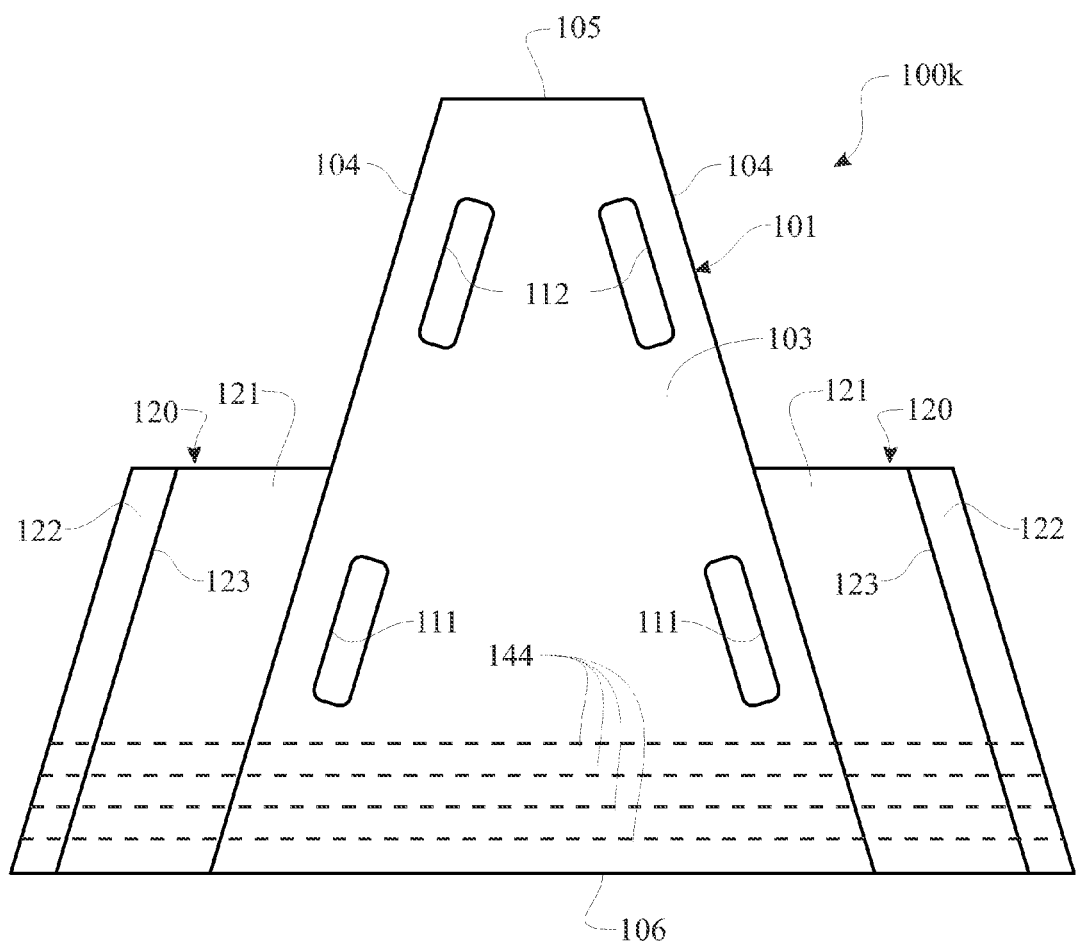
FIG. 18 is a top view of another alternative illustrative embodiment of the heel offloading leg abductor pillow.

Referring next to FIG. 18 of the drawings, another alternative illustrative embodiment of the heel offloading leg abductor pillow 100*k* includes multiple perforations 144 which extend transversely across the proximal pillow body 101 and each distal leg support portion 120, generally parallel and adjacent to the distal end 106 of the pillow body 101 and each other. Accordingly, the proximal pillow body 101 and each leg support portion 120 can be selectively cut along one of the perforations 144 to yield a heel offloading leg abductor pillow 100*k* having a length which may be selected according to the length of the patient's legs 133 (FIG. 8), for example.

The distance between the bottom surface 102 and the lower apex of the leg trough 123 can be varied by stacking layers or spacing members between the pillow body 101 and a separating version of the pillow body base 101*a*. Optionally, the heel offloading leg abductor pillow 100 can incorporate a bottom surface 102 that is tapered, having a distance between the bottom surface 102 and the lower apex of the leg trough 123 that increases moving from the proximal end 105 towards the distal end 106. This configuration elevates the patient's feet above the knee and waist.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

I claim:

1. A heel offloading abductor pillow, comprising:
    a generally resilient, wedge-shaped unitary pillow body having a perimeter defined by a top surface, a bottom surface, a proximal end, a first side surface having a first side elongated attachment slot, a distal end and a second side surface having a second side elongated attachment slot, wherein a distance between ends of the first side surface and the second side surface adjacent to the proximal end is shorter than a distance between ends of said first side surface and said second side surface adjacent to the distal end; and
    a pair of leg support portions, each leg support portion comprising an elongated leg support inner sidewall located along a side portion of a leg support bottom, a concave upper leg support surface formed along a length of an upper surface of the leg support, wherein the upper surface length is equal to a distance measured between the pillow body distal end and a location approximately midway between the proximal and distal end, and an attachment tab extending laterally outward from said elongated leg support inner sidewall, each leg support portion attachment tab slideably engages within first and second side elongated attachment slots, respectively, wherein each said leg support portion extends laterally outward from and primarily structurally supported by said pillow body.

2. The heel offloading abductor pillow of claim 1 wherein said pillow body comprises a bottom surface and a top surface, and further comprising an elevation wedge provided on said bottom surface of said pillow body.

3. The heel offloading abductor pillow of claim 2 wherein said bottom surface of said pillow body is generally convex.

4. The heel offloading abductor pillow of claim 3 further comprising a resilient pillow base and wherein said bottom surface of said pillow body is seated in said pillow base.

5. The heel offloading abductor pillow of claim 3 wherein said pair of leg support portions each has a generally convex bottom surface.

6. The heel offloading abductor pillow of claim 2 further comprising a hinge provided transversely in said pillow body.

7. The heel offloading abductor pillow of claim 1 each leg support inner sidewall further comprises a generally vertical segment extending upward from and being continuous with a first edge of said leg trough and an outer sidewall defined as a generally vertical segment extending upward from and being continuous with a second edge of said leg trough, said first edge located opposite said second edge of said leg trough.

8. The heel offloading abductor pillow of claim 1 further comprising a plurality of perforations provided in said pillow body and said pair of leg support portions generally parallel and adjacent to said distal end of said pillow body and each other.

9. A heel offloading abductor pillow, comprising:
    a generally resilient, wedge-shaped unitary pillow body having a perimeter defined by a top surface, a bottom surface, a proximal end, a first side surface, a distal end and a second side surface wherein a distance between ends of the first side surface and the second side surface adjacent to the proximal end is shorter than a distance between ends of said first side surface and said second side surface adjacent to the distal end; and
    a pair of leg support portions, each leg support portion extending laterally outward from and primarily structurally supported by said pillow body, each leg support portion having a length extending from the pillow body distal end towards the pillow body proximal end, the leg support portions each terminating approximately midway between the proximal and distal end, each leg support portion having a leg support bottom surface coplanar with said pillow body bottom surface, and each leg support portion having a concave upper leg support surface, said concave upper leg support surface bounded by a leg support outer sidewall and a respective one of said first and second pillow body side surfaces.

10. The heel offloading abductor pillow of claim 9, wherein the pair of leg support portions are removably attached to the wedge-shaped pillow body.

11. The heel offloading abductor pillow of claim 10, wherein the pair of leg support portions provided within a pillow base body, wherein said pillow base body is defined by a planar mid section and two outer leg support sections, the pillow base body being removably attached to a bottom of the wedge-shaped pillow body.

12. The heel offloading abductor pillow of claim 9 further comprising a proximal strap opening and a pair of spaced-apart distal strap slots extending through said pillow body, and a pair of proximal leg straps extending through said proximal strap opening and a pair of distal leg straps extending through said pair of distal strap slots, respectively.

13. The heel offloading abductor pillow of claim 9 further comprising a pair of spaced-apart proximal strap slots and a pair of spaced-apart distal strap slots extending through said pillow body; and a pair of proximal leg straps extending through said proximal strap slots, respectively, and a pair of distal leg straps extending through said pair of distal strap slots, respectively.

14. The heel offloading abductor pillow of claim 9 further comprising a proximal cavity provided in said proximal end of said pillow body.

15. The heel offloading abductor pillow of claim 9 wherein each of said pair of leg support portions is integral with said pillow body.

16. The heel offloading abductor pillow of claim 9 wherein each of said pair of leg support portions is positionally adjustable on said pillow body.

17. A heel offloading abductor pillow, comprising:
- a generally elongated, resilient, wedge-shaped unitary pillow body having a perimeter defined by a top surface, a bottom surface, a proximal end, a first side surface, a distal end and a second side surface wherein a distance between the ends of the first side surface and the second side surface adjacent to the proximal end is shorter than a distance between the ends of the first side surface and the second side surface adjacent to the distal end;
- a pair of leg support portions, each leg support portion extending laterally outward from and primarily structurally supported by said pillow body, each leg support portion having a length extending from the pillow body distal end towards the pillow body proximal end, the leg support portions each terminating approximately midway between the proximal and distal end, each leg support portion having a leg support bottom surface coplanar with said pillow body bottom surface, and each leg support portion having a concave upper leg support surface, said concave upper leg support surface bounded by a leg support outer sidewall and a respective one of said first and second pillow body side surfaces,
- a proximal strap opening located through said pillow body at a location between said proximal pillow body end an initial surface of each said leg support portions; and
- a proximal leg strap inserted through said proximal strap opening and extends about said side surface for securing a patient's unsupported leg to said side surface.

18. The heel offloading abductor pillow of claim 17 wherein each of said pair of leg support portions comprises a leg support bottom and a leg support outer sidewall defined as a generally vertical segment extending upward from and being continuous with an outer edge of said concave leg support surface.

19. The heel offloading abductor pillow of claim 18 wherein each of said pair of leg support portions has a generally rounded cross-sectional shape.

20. The heel offloading abductor pillow of claim 17 wherein a bottom surface of the heel offloading abductor pillow is at least partially curved aiding in rolling a patient's lower extremities.

21. The heel offloading abductor pillow of claim 17, the pillow additionally comprising a foot drop strap located at a distal end of said concave leg support surface, the foot drop strap providing support of a patient's heel.

\* \* \* \* \*